United States Patent [19]

Osborne

[11] E Patent Number: Re. 31,855

[45] Reissued Date of Patent: Mar. 26, 1985

[54] TEAR APART CANNULA

[75] Inventor: Thomas A. Osborne, Bloomington, Ind.

[73] Assignee: Cook, Inc., Bloomington, Ind.

[21] Appl. No.: 443,321

[22] Filed: Nov. 22, 1982

Related U.S. Patent Documents

Reissue of:

[64] Patent No.: 4,306,562
Issued: Dec. 22, 1981
Appl. No.: 173,960
Filed: Jul. 31, 1980

U.S. Applications:

[63] Continuation of Ser. No. 965,703, Dec. 1, 1978, abandoned.

[51] Int. Cl.[3] ..... A61M 25/00

[52] U.S. Cl. ..... 604/161; 604/164

[58] Field of Search ..... 604/158-172; 128/784

[56] References Cited

U.S. PATENT DOCUMENTS

| | | | |
|---|---|---|---|
| 3,094,122 | 6/1963 | Gauthier et al. | 128/271 |
| 3,094,124 | 6/1963 | Birtwell | 128/348 |
| 3,166,688 | 1/1965 | Rowland et al. | 128/348 |
| 3,225,762 | 12/1965 | Guttman | 128/214 |
| 3,382,872 | 5/1968 | Rubin | 128/214.4 |
| 3,469,579 | 9/1969 | Hubert | 128/221 |
| 3,545,443 | 12/1970 | Ansari | 128/347 |
| 3,550,591 | 12/1970 | MacGregor | 128/214.4 |
| 3,570,485 | 3/1971 | Reilly | 128/214.4 |
| 3,598,118 | 8/1971 | Warren | 128/214.4 |
| 3,677,243 | 7/1972 | Nerz | 128/214.4 |
| 3,877,429 | 4/1975 | Rasumoff | 128/321 |
| 4,054,136 | 10/1977 | Von Zeppelin | 604/160 |
| 4,166,469 | 9/1979 | Littleford | 128/784 |

FOREIGN PATENT DOCUMENTS 2104226 12/1971 Fed. Rep. of Germany .

OTHER PUBLICATIONS

"High Quality Hose Constructions From Teflon TFE Fluorocarbon Resins", *DuPont Tech. Services Laboratory*, Ribbans, TR#138.

"Percutaneus Insertion of a Permanent Transvenous Pacemaker Electrode Through the Subclavian Vein" *Can. J. Surgery*, Friesen et al., 3-77, pp. 131-135.

Article-"Eine Neue Methode zur Perkutanen Implantation permaneter Herz Schritt Macher", (A New Method for the Percutaneous Implantation of Permanent Pacemakers) by H. Sterz et al. (with translation).

*Primary Examiner*—Benjamin R. Padgett
*Assistant Examiner*—T. J. Wallen
*Attorney, Agent, or Firm*—Woodard, Weikart, Emhardt & Naughton

[57] ABSTRACT

This invention relates to a flexible cannula comprising material which tears readily in a longitudinal direction and can thus be easily removed by pulling tabs on opposite sides of the cannula apart after the catheter or other device has been inserted into the body.

16 Claims, 18 Drawing Figures

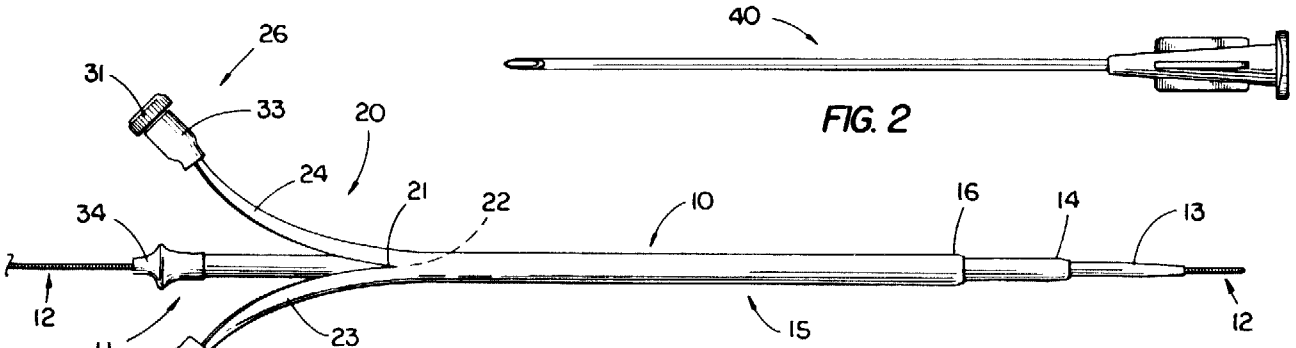
FIG. 2
FIG. 1
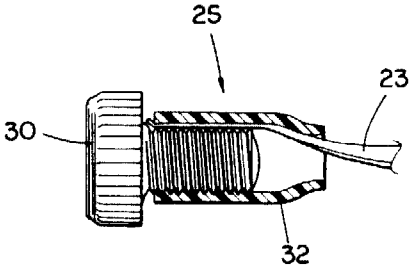
FIG. 1B
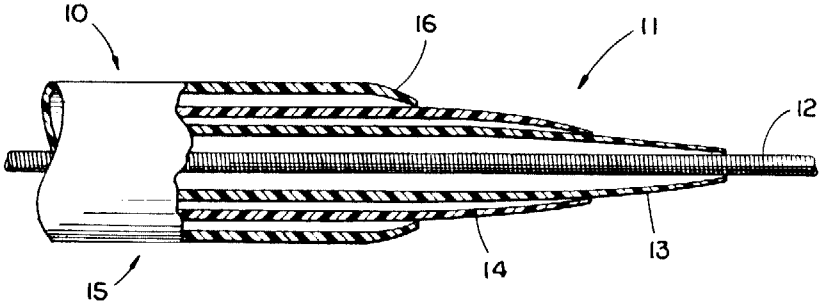
FIG. 1A

TEAR APART CANNULA

Matter enclosed in heavy brackets [ ] appears in the original patent but forms no part of this reissue specification; matter printed in italics indicates the additions made by reissue.

This is a continuation, of application Ser. No. 965,703 filed Dec. 1, 1978, now abandoned.

BACKGROUND OF THE INVENTION

1. Field of the Invention

This invention relates generally to a cannula used as an aid for insertion of catheters and other instruments into the body and more particularly to a cannula that is easily removed after the insertion is completed.

2. Brief Description of the Prior Art

It is desirable that after a catheter or other body probe device has been inserted into place within a blood vessel that the apparatus used to aid the insertion is easily removable. When sharp devices such as hollow needles are left in place while the catheter or other device is being utilized, there is a danger that the needle may pierce through the vessel, causing tissue damage and rendering the catheter useless. In assemblies where the needle is removable, this problem is alleviated; however, in these cases, the cannula which is used as a passageway into the blood vessel, often cannot itself be easily removed when the probe or catheter that has been inserted has an enlarged proximal end. The inability to easily remove the cannula is a disadvantage in circumstances when the inserted probe or catheter must remain in the body for an extended period of time to be permanently implanted.

Various removable devices have been developed using frangible, hollow needles (see Rubin, U.S. Pat. No. 3,382,872; MacGregor, U.S. Pat. No. 3,550,591; Warren, U.S. Pat. No. 3,598,118 and Nerz, U.S. Pat. No. 3,677,243). In these devices the hollow needle must have a larger diameter to accommodate the catheter within the device. The larger size of the hollow needles can be a cause of additional tissue damage. Because of their rigidity and sharpness, these needles act as poor cannuli in situations where probes must be inserted and removed repeatedly, and they cannot be used at all when the cannula must be used as an aid in advancing the probe along the interior of the blood vessel.

Ansari, U.S. Pat. No. 3,545,443, utilizes dual hollow concentric needles, each having a longitudinal slot. After insertion, the needle assembly is removed and twisted in such a manner that the slots are aligned. The catheter then can pass through the slots thus removing the needle. This non-frangible assembly possesses many of the same disadvantages that the other hollow needle devices have. In addition, because there are two hollow needles, an even larger needle diameter is necessary to accomodate the same size catheter. The slots in the needles may also cause additional tissue damage and potentially may not be able to effectively prevent blood loss and air emboli.

Gauthier, U.S. Pat. No. 3,094,122, uses a percutaneous needle that is inside the catheter. After insertion, the needle is removed lengthwise from the catheter. There are several restrictions upon this method. The needle must be longer than the catheter and the method is only adaptable for insertion of hollow devices or catheters and cannot be used where various probes and leads are to be inserted. Guttman, U.S. Pat. No. 3,225,762, is similar to the Gauthier device except that the catheter has a slot for removal of the needle after insertion. This eliminates the need to have a needle that is longer than the catheter, however, there may be undesirable leakage through the slit, particularly when the catheter is bent at or near the slit. This invention also cannot be used where the probe to be inserted within the vessel is not hollow.

Reilly, U.S. Pat. No. 3,570,485, provides a flexible cannula, placed over the percutaneous needle, that is slotted along its length. After insertion, the needle is removed and the cannula can then act as a sheath for insertion of the catheter or other device. After insertion of the probe, the cannula can be removed by sliding the catheter or other device through the slit in the cannula. Although this invention is flexible and can be adopted for insertion of both catheters and non-hollow probes, the longitudinal slot may not provide a blood or airtight seal. This problem may be reduced by increasing the thickness of the cannula, however this would necessitate either the use of a larger puncture diameter or a smaller probe. Further, removal of the cannula requires gripping both the cannula and the inserted catheter and physically pulling them apart. Applying such a force upon an object that is partially inserted into the body may cause tissue damage. There is also the potential of accidentally pulling the catheter out from its inserted position.

The Reilly patent has a further limitation in its collapsibility. When the Reilly cannula is empty prior to insertion of the catheter or probe, it collapses upon itself at the puncture site with the purpose of preventing blood loss. However, this attribute creates a disadvantage in that a stiff catheter with a stiff tapered distal end is required in order to reopen the cannula for reinsertion; therefore, flimsy and flexible leads, such as pacemaker leads and blunted tipped catheters, such as balloon tipped catheters, are unadoptable for use with this device.

BRIEF DESCRIPTION OF THE PRESENT INVENTION

The present invention is a flexible cannula that readily tears in a longitudinal direction along the length of the structure because it comprises material that has a longitudinal orientation. Because it is flexible and hollow, it acts as a good cannula where devices must be repeatedly inserted, left within the body for a period of time, or advanced along the interior of the vessel.

Because of its longitudinal orientation, the present invention can readily be removed by tearing the structure along its length along two longitudinal lines thereby splitting it into two halves. This is a particular advantage where the lead or probe is to be permanently inserted and has large fittings or connectors on its proximal end such that the cannula cannot merely be slipped off the end of the probe.

Because no force needs to be applied to the partially inserted probe when the cannula is split apart, the potential of accidentally pulling the probe out from its desired position is diminished.

There are numerous specific applications in which the present invention can be utilized. One such application is for suprapubic insertion into the bladder. Catheters used in this type of application normally have enlarged proximal ends and remain in the body for prolonged periods of time.

Another application is transvenous insertion of permanent pacemaker leads. Such leads separate into various electrodes at the proximal end, each electrode being significantly larger than the general diameter of the lead. After insertion of the distal end into the desired position within the heart. These leads must themselves be implanted beneath the skin and connected to a power source. In the past, it has been the practice to remove the sheath by slitting it with a scapel, in order to enable the implantation of the electrodes. Reference is made to "Percutaneous Insertion of a Permanent Transvenous Pacemaker Electrode through the Subclavion Vein" in the Canadian Journal of Surgery, vol. 20, pg. 131 which is descriptive of this technique.

There are several existing techniques which can take advantage of the benefits of the present invention. In one method the cannula is inserted into a blood vessel about percutaneous needle. The needle is then removed, and a catheter or other probe device is inserted through the sheath and the combination is advanced into position. The cannula can then be slipped out of the body and split by pulling a pair of tabs on the end thereof thus being removed from the probe.

In another method, a hollow needle is inserted into a vessel. A wire guide is then passed through the needle into the interior portion of the vessel. The needle can then be withdrawn and the cannula with a dilator inserted into the vessel over the wire guide. The assembly is advanced into position and the dilator and wire guide are removed. A catheter or probe can next be passed into the vessel through the cannula. The cannula is withdrawn from the body and split apart thus being removed from about the probe.

BRIEF DESCRIPTION OF THE DRAWINGS

FIG. 1 is a side view of the splitable cannula in combination with a dilator and wire guide.

FIG. 1A is an enlarged view similar to FIG. 1 of the structure of FIG. 1 with portions broken away to show internal structure.

FIG. 1B is an enlarged fragmentary view of a portion of the structure of FIG. 1.

FIG. 2 is a side view of a hollow percutaneous needle.

FIG. 3 illustrates the needle inserted within the blood vessel.

FIG. 4 shows a wire guide inserted into the vessel through the incision needle.

FIG. 5 shows the incision withdrawn from the puncture site.

FIG. 6 shows the wire guide percutaneously positioned within the blood vessel.

FIG. 7 illustrates the splitable sheath and dilator combination inserted into the vessel over the wire guide.

FIG. 8 illustrates the guide dilator and splitable cannula assembly advanced into the desired position within the vessel.

FIG. 9 shows the splitable cannula in position after the wire guide and dilator have been removed.

FIG. 10 illustrates a probe inserted within the splitable cannula.

FIG. 11 shows the cannula after being split into two parts.

FIG. 12 illustrates a splitable cannula disposed about the incision needle and inserted in this manner into the blood vessel.

FIG. 13 shows the splitable cannula inserted within the vessel after the incision needle has been removed.

FIG. 14 illustrates the probe inserted within the cannula.

FIG. 15 shows the probe and splitable cannula combination advanced into the desired position within the vessel.

FIG. 16 illustrates the cannula split into two parts.

DETAILED DESCRIPTION OF THE PREFERRED EMBODIMENT

Figure 3:
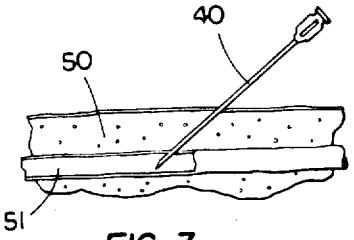
FIG. 3 through FIG. 11 are sections through a blood vessel showing a procedure.

A preferred embodiment of the present invention is shown in combination with a dilator and a wire guide in FIG. 1. The splitable cannula 10 is disposed about the dilator 11 which, in turn, is disposed about the wire guide 12. The distal end 13 of the dilator is tapered for enlarging the puncture site to accommodate the splittable cannula. Where the diameter of the splittable cannula is of a sufficiently large size, the dilator that is used has a second tapered portion 14. The tubular portion 15 of the splittable cannula has approximately uniform thickness and diameter except at its distal end 16 where there is a slight taper to create an appropriately snug fit with the dilator and also to facilitate the enlarging of the puncture site to accommodate the cannula. The proximal end 20 of the cannula is slit longitudinally producing two open ended slits at opposite sides of the tubular structure 21 and 22, thus creating two tabs 23 and 24 which are attached to knobs 25 and 26 by being inserted between the screw 30 and 31 and socket 32 and 33 portions of the knobs. At the proximal end of the dilator 11 is a knob-like clamp 34 which maintains the two telescoping layers of the dilator 11 in position.

FIG. 1B is a cross-sectional view showing a representative one of the tabs 23 attached to one of the knobs 25 which comprises a screw 30 and socket 32 combination. The screw 30 is screwed into the socket 32 with the end 23 in the socket. The force between the screw 30 and socket 32 maintains the end of the tab in position. The knobs 25 and 26 are used to aid in gripping the device when it is split apart.

FIGS. 3 through FIG. 11 shows a procedure whereby a probe having relatively large fittings on its proximal end is placed in position. The probe might be, for example, a catheter used to measure the flow of saline solution through the blood vessel. Such catheters have a balloon at the distal end which operates to close off the flow through the blood vessel. This balloon is inflated by placing air into a fitting such as the fitting 61. Another fitting such as fitting 62 might receive the saline solution. Still another fitting such as the fitting 63 functions to provide a coupling to a thermistor which measures the temperature of the saline solution blood mixture as it moves by the thermistor at still another point along the catheter.

Figure 4:
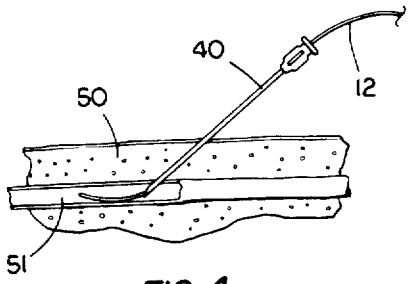
Figure 5:
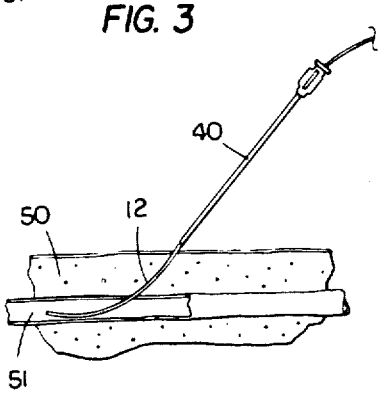
Figure 6:
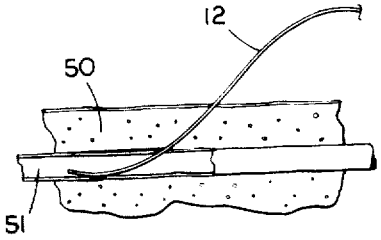
Figure 7:
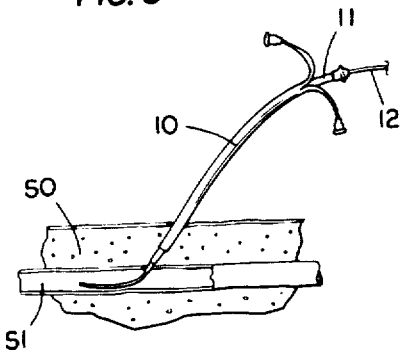
Figure 8:
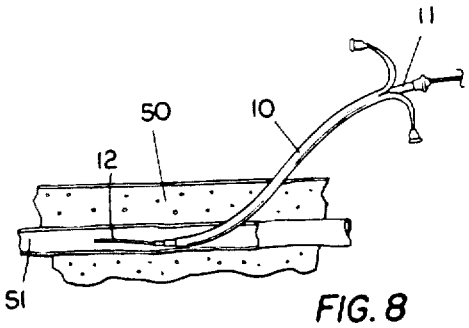
Figure 9:
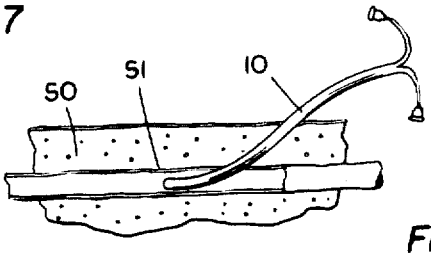
Figure 10:
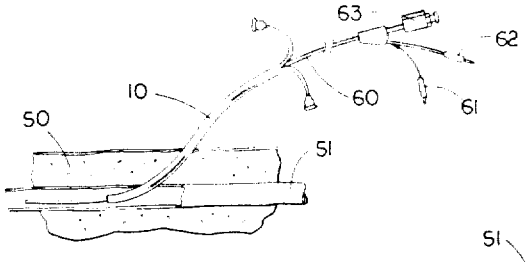
Figure 11:
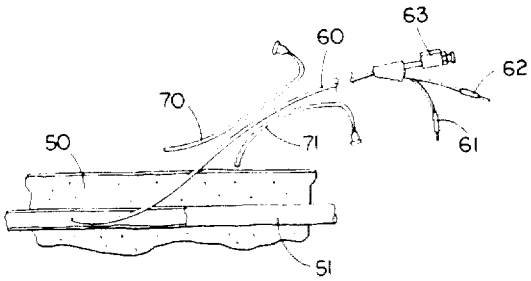

FIG. 3 shows the percutaneous needle 40 inserted through the skin and body tissue 50 and into a blood vessel 51. FIG. 4 shows the subsequent step of inserting the wire guide 12 into the blood vessel 51 through the needle 40. In FIG. 5 the needle 40 has been removed from the puncture site leaving the wire guide as in FIG. 6. In FIG. 7 the splitable cannula 10 and dilator 11 combination is in the process of being inserted into the blood vessel 51 about the wire guide 12. The cannula, dilator and wire guide combination have been advanced into the desired position in FIG. 8. In FIG. 9 the wire guide and dilator have been removed leaving the splittable cannula 10 in its desired position. FIG. 10 shows a probe 60 being inserted into the blood vessel through the splitable cannula 10. The probe elements 61, 62 and 63 are fittings which are permanently mounted on the proximal end of the probe 60. In FIG. 11 the splittable cannula has been removed from the puncture site and split apart into two portions 70 and 71 and in this manner has been separated from the inserted probe.

Figure 12:
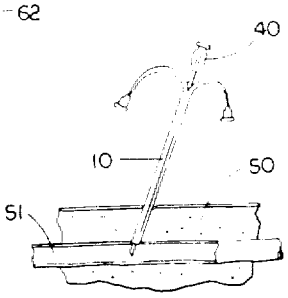
FIG. 12 through FIG. 16 are sections through a blood vessel showing a further procedure.
Figure 13:
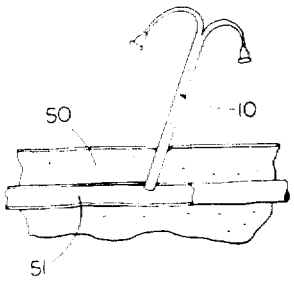
Figure 14:
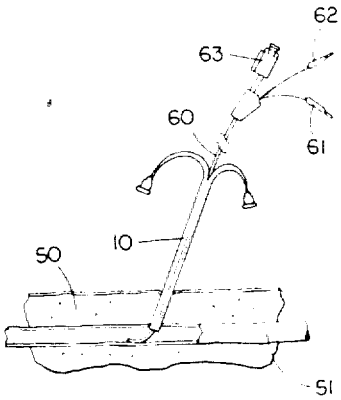
Figure 15:
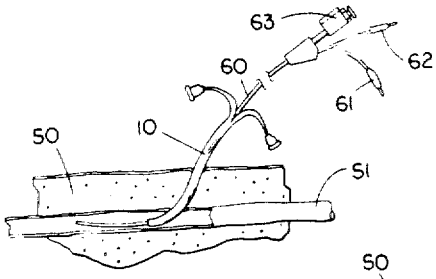
Figure 16:
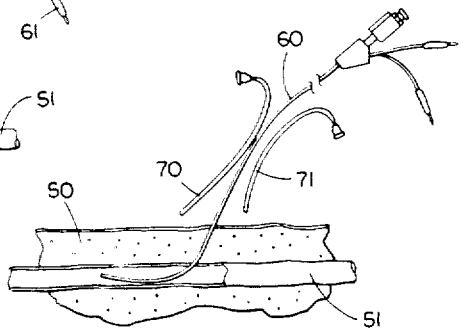

In an alternative technique, the splittable cannula 10 may be inserted within the blood vessel 50 directly about the needle 40. FIG. 12 shows this combination inserted within the blood vessel. FIG. 13 illustrates the splitable cannula 10 inserted within the blood vessel after the incision needle 40 has been removed from the puncture site. FIG. 14 illustrates the probe 60 introduced into the blood vessel 51 through the splittable cannula 10. In FIG. 15 the probe 60 and cannula 10 combination have been advanced into position. FIG. 16 shows the cannula 10 withdrawn and split off leaving the probe in position.

Teflon (Teflon is the Dupont trademark for polytetrafluoroethylene) used in the preferred embodiment is virgin material i.e., has not previously been used, or reground. It is free of foreign matter and dye marks. These characteristics are required to ensure compatibility for insertion into the body. Teflon is the preferred material because it can be longitudinally oriented through extrusion, although other plastics may be useable. It is known, for example, that polyethylene obtains the required longitudinal orientation characteristics if it is stretched after extrusion. However, polyethylene is not used in the preferred embodiment because it is understood that the orientation process for polyethylene is more difficult to perform properly.

A standard extrusion process orientates the Teflon and forms it into the tubular shape of the cannula. The Teflon is blended with an extrusion aid or lubricant, preferably naphtha, and a thermally stable pigment. The pigment used may be any stable pigment that is acceptable for insertion within the body. The naphtha normally comprises between 17 and 20% by weight and the concentration of pigment should be less than 2%. Then, at temperatures above 75° F., the compound mixture is preformed. The object of preforming is to compact the powder into a cylinder which is about one-third of the original volume. The preforming pressure is between 100 and 300 lbs/sq. in. The preform is then extruded through an extrusion die at pressures of approximately 20,000 psi. After extrusion the Teflon tubing is passed through a drying oven at a graduated temperature increasing from 300° F. to 575° F. The heat from this oven vaporizes the lubricant. The Teflon tubing is next led through a sintering oven, at temperatures of at least 621° F., allowed to cool, and rolled onto spools.

In the manufacturing of the cannula, the Teflon tubing is cut off radially to define one end of the cannula and slit at that one end with a cutting instrument at opposite ends of the same end to form the two opposed slits 20 and 21. This slitting operation creates the tabs 23 and 24 which are used to pull apart the cannula and the slits define the location of the beginning of the tears when the tabs are pulled. A screw and socket combination 25 and 26 is attached to each tab, as illustrated in FIG. 1B, to facilitate the gripping and pulling of the tabs.

An appropriate length is then measured and a heat gun applied to the tubing. Upon application of this heat, the tubing is stretched, yielding a tapered end. The tip is then cut at a point where the inside diameter of the cannula approximates the outside diameter of the dilator which will be used with the particular cannula. This tapering method serves two purposes. First, the outside diameter is tapered to facilitate insertion of the cannula into the body. Second, a tight fit with the probe at this end minimizes blood loss.

In one preferred embodiment of the present invention, the thickness of the structure from the inner surface to the outer surface is 0.010 inch with a tolerance of plus or minus 0.002 inch. The required diameter of the cannula will vary with the diameter of various dilators which are used in combination with the sheath. It is estimated that useful sizes will range from an inner diameter of 0.05 inch to an inner diameter of 0.2 inches; however, there may be applications requiring larger or smaller dimensions. The inner diameter tolerance is plus 0.002 inch and minus 0.000 inch.

In the preferred embodiment, the cannula is sterilized using ethylene oxide and packaged with a sterilized percutaneous needle, a wire guide, and a dilator in a hermetically sealed plastic bag.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

The invention claimed is:

1. A cannula comprising a tubular structure having one end which has a pair of open ended slits, said tubular structure being compatible for insertion within the body and having an opposite end adapted to be inserted in the body with said one end extending out of the body, said tubular structure being formed of flexible material having the physical property of molecular orientation whereby a tear in said material runs readily only in a longitudinal direction along the length of said tubular structure, said tubular structure being flexible from its inner diameter to its outer diameter and continuously smooth on its inner surface and outer surface, said slits each having a closed end located between said one end and said opposite end;

a first tab defined by said slits on one side of one end of said tubular structure; and a second tab defined by said slits on the other side of said one end of said tubular structure whereby when said tabs are pulled apart, said structure tears longitudinally along its length beginning at said closed ends and extending to the opposite end of said tubular structure.

2. The cannula of claim 1 in which the flexible material is a plastic.

3. The cannula of claim 1 in which the flexible material is polytetrafluoroethylene.

4. The cannula of claim 1 in which said opposite end is tapered so as to define a tapered end portion, said tubular structure having an inner surface and an outer surface and having a substantially uniform thickness from the inner surface to the outer surface except at the tapered portion.

5. The cannula of claim 1 in which said tabs are integral with said tubular structure and are separated by said open ended slits.

6. A cannula kit comprising:

a cannula including a tube of flexible material having the physical property of molecular orientation whereby a tear in said material runs readily only in a longitudinal direction along the length of the tube, said tube being soft and flexible from its inner diameter to its outer diameter; a first tab on one side of one end of said tube, a second tab on the other side of said one end of said tube whereby, when said tabs are pulled apart, said tube tears longitudinally separating said tube from any object within said tube;

a percutaneous needle;

a wire guide;

a dilator;

and a bag containing said cannula, guide and dilator.

7. The cannula kit of claim 6 where said bag is hermetically sealed and made of plastic.

8. A cannula comprising:

a tubular structure having one end which has a pair of open ended slits, said tubular structure being compatible for insertion within the body and having an opposite end adapted to be inserted in the body with said one end extending out of the body, said tubular structure being continuously smooth on its inner surface and outer surface, means for allowing the opposite end to remain continuously smooth on its inner surface and outer surface while the opposite end is within the body, said means for allowing including said tubular structure being formed of flexible material having the physical property of molecular orientation whereby a tear in said material runs readily only in a longitudinal direction along the length of said tubular structure, a first tab defined by said slits on one side of said one end of said tubular structure; and a second tab defined by said slits on the other side of said one end of said tubular structure whereby, when said tabs are pulled apart, said structure tears longitudinally along its length beginning at said slit closed ends and extending to the opposite end of said tubular structure.

9. A removable cannula for introducing a member into an internal organ of the body, said cannula comprising:

(a) a tubular structure compatible for insertion within the body, said tubular structure having one end and having an opposite end adopted to be inserted into the body with said one end extending out of the body, said tubular structure being flexible from its inner diameter to its outer diameter, said tubular structure having an internal passageway for passage of a member into an internal organ of the body; and (b) removal means for removing said cannula from about the member after the introduction of the member into the body through the internal passageway of said tubular system, said removal means including means for providing for the inserted portion of said tubular structure to remain continuously smooth on its inner surface and its outer surface during insertion, said removal means including:

(i) said flexible material having the physical property of molecular orientation whereby a tear in said material runs readily only in a longitudinal direction along the length of said tubular structure, (ii) said one end of said tubular structure having a pair of open ended slits, said slits having closed ends located between said one end and said opposite end, (iii) a first tab defined by said slits on one side of said one end of said tubular structure and (iv) a second tab defined by said slits on the other side of said one end of said tubular structure whereby, when said tabs are pulled apart, said structure tears longitudinally along its length beginning at said closed ends of said slits and extending to the opposite end of said tubular structure.

*10. A cannula kit comprising:*

*a tube of flexible plastic material compatible for insertion within the body and having the physical property of molecular orientation whereby a tear in said material runs readily only in a longitudinal direction along the length of the tube, said tube being soft and flexible from its inner diameter to its outer diameter; a first tab on one side of one end of said tube, and a second tab on the other side of said one end of said tube whereby, when said tabs are pulled apart, said tube tears longitudinally separating said tube from any object within said tube; and a dilator.*

*11. A cannula comprising:*

*a tube of flexible material compatible for insertion within the body and having the physical property of molecular orientation allowing a tear in said material to run readily only in a longitudinal direction along the length of the tube, said tube being soft and flexible from its inner diameter to its outer diameter and tapered at one end adapted for insertion within the body; a first tab on one side of the end of said tube opposite said one end and a second tab on the other side of said opposite end of said tube whereby, when said tabs are pulled apart said tube tears longitudinally separating said tube from any object within said tube.*

*12. The cannula of claim 11 wherein said tube is continuously smooth on its outer surface.*

*13. The cannula of claim 12 wherein said tube is continuously smooth on its inner surface.*

*14. A cannula comprising:*

*a tubular structure having one end which has a pair of open ended slits, said tubular structure being compatible for insertion within the body and having an opposite end adapted to be inserted in the body with said one end extending out of the body, said tubular structure being formed of flexible material having the physical property of molecular orientation allowing a tear in said material to run readily only in a longitudinal direction along the length of said tubular structure, said tubular structure being flexible from its inner diameter to its outer diameter, said slits each having a closed end located between said one end and said opposite end;*

*a first tab defined by said slits on one side of one end of said tubular structure; and*

*a second tab defined by said slits on the other side of said one end of said tubular structure whereby when said tabs are pulled apart, said structure tears longitudinally along its length beginning at said closed ends*

*and extending to the opposite end of said tubular structure without the need for any mechanical means for facilitating longitudinal separation of said tube.*

*15. The cannula of claim 14 in which said tubular structure is continuously smooth on its outer surface.*

*16. A cannula comprising: a tube of flexible plastic material compatible for insertion within the body and having the physical property of molecular orientation whereby a tear in said material runs readily only in a longitudinal direction along the length of the tube, said tube including a non-mechanical means for longitudinally tearing apart said tube, said tube being soft and flexible from its inner diameter to its outer diameter; a first tab on one side of one end of said tube, and a second tab on the other side of said one end of said tube whereby, when said tabs are pulled apart, said tube tears longitudinally solely due to said non-mechanical means, separating said tube from any object within said tube.*

* * * * *

UNITED STATES PATENT AND TRADEMARK OFFICE

CERTIFICATE OF CORRECTION

PATENT NO. : Re. 31,855

DATED : March 26, 1985

INVENTOR(S) : Thomas A. Osborne

It is certified that error appears in the above-identified patent and that said Letters Patent is hereby corrected as shown below:

In column 5, line 61, replace "ends" with --sides--.

In column 7, line 11, replace "tube, a" with --tube, and a--.

In column 7, line 19, after "cannula," insert --needle,--.

In column 8, line 43, after "longitudinally" insert --, solely due to said tube's physical property of molecular orientation,--.

Signed and Sealed this

Twenty-fifth Day of August, 1987

*Attest:*

DONALD J. QUIGG

*Attesting Officer*

*Commissioner of Patents and Trademarks*

REEXAMINATION CERTIFICATE (557th)

United States Patent [19] [11] B1 Re. 31,855

Osborne [45] Certificate Issued Aug. 19, 1986

[54] TEAR APART CANNULA

[75] Inventor: Thomas A. Osborne, Bloomington, Ind.

[73] Assignee: Cook, Inc., Bloomington, Ind.

Reexamination Request:
No. 90/000,797, Jun. 13, 1985

Reexamination Certificate for:

| | |
|---|---|
| Patent No.: | **Re. 31,855** |
| Issued: | **Mar. 26, 1985** |
| Appl. No.: | **443,321** |
| Filed: | **Nov. 22, 1982** |

Related U.S. Patent Documents

Reissue of:

| | | |
|---|---|---|
| [64] | Patent No.: | **4,306,562** |
| | Issued: | **Dec. 22, 1981** |
| | Appl. No.: | **173,960** |
| | Filed: | **Jul. 31, 1980** |

U.S. Applications:

[63] Continuation of Ser. No. 965,703, Dec. 1, 1978, abandoned.

[51] Int. Cl.[4] ..... A61M 5/18
[52] U.S. Cl. ..... 604/161; 604/164
[58] Field of Search ..... 604/158-172; 128/784

[56] References Cited

U.S. PATENT DOCUMENTS

| | | | |
|---|---|---|---|
| Re. 30,726 | 9/1981 | Otten et al. | 206/601 |
| 2,105,367 | 1/1938 | Parsons | 229/87 |
| 2,128,374 | 5/1938 | Midulla | 131/11 |
| 2,329,360 | 9/1943 | Salfisberg | 229/51 |
| 2,456,621 | 12/1948 | Cheney | 18/59 |
| 2,685,707 | 8/1954 | Llewellyn | 18/55 |
| 2,752,637 | 7/1956 | Walker et al. | 18/55 |
| 2,776,465 | 1/1957 | Smith | 28/82 |
| 3,008,187 | 11/1961 | Slade | 18/14 |
| 3,034,941 | 5/1962 | Hessenthaler et al. | 154/46 |
| 3,094,122 | 6/1963 | Gauthier et al. | 128/221 |
| 3,094,124 | 6/1963 | Birtwell | 128/348 |
| 3,166,688 | 1/1965 | Rowland et al. | 317/2 |
| 3,175,752 | 3/1965 | Stabenow | 229/51 |
| 3,180,909 | 4/1965 | Looser | 264/95 |
| 3,223,762 | 12/1965 | Fry, Jr. | 264/95 |
| 3,225,762 | 12/1965 | Guttman | 128/214 |
| 3,244,781 | 4/1966 | Covington et al. | 265/95 |
| 3,302,856 | 2/1967 | Thompson et al. | 229/51 |
| 3,333,682 | 8/1967 | Burke | 206/43 |
| 3,344,975 | 10/1967 | Stoker | 229/51 |
| 3,368,740 | 2/1968 | Rohde | 229/66 |
| 3,382,872 | 5/1978 | Rubin | 128/214.4 |
| 3,404,203 | 10/1968 | Donald | 264/108 |
| 3,469,579 | 9/1969 | Hubert | 128/214.4 |
| 3,545,443 | 12/1970 | Ansari | 128/214.4 |
| 3,550,591 | 12/1970 | MacGregor | 128/214.4 |
| 3,570,485 | 3/1971 | Reilly | 128/214.4 |
| 3,577,258 | 5/1971 | Sincavage et al. | 117/62 |
| 3,598,118 | 8/1971 | Warren | 128/214.4 |
| 3,608,815 | 9/1971 | Bunch | 229/66 |
| 3,677,243 | 7/1972 | Nerz | 128/214.4 |
| 3,877,429 | 4/1975 | Rasumoff | 128/214.4 |
| 3,899,283 | 8/1975 | Wallis | 425/461 |
| 3,980,224 | 9/1976 | Yasuda | 229/51 TS |
| 4,049,761 | 10/1977 | Lorgé et al. | 264/89 |
| 4,054,136 | 10/1977 | von Zepplin | 128/214.4 |
| 4,056,418 | 11/1977 | Aspin | 156/145 |
| 4,098,406 | 7/1978 | Otten et al. | 206/601 |
| 4,150,184 | 4/1979 | Tesch | 428/43 |
| 4,166,469 | 9/1979 | Littleford | 128/784 |
| 4,386,705 | 6/1983 | Meuller | 206/626 |

FOREIGN PATENT DOCUMENTS 2104226 12/1971 Fed. Rep. of Germany .

OTHER PUBLICATIONS

"High Quality Hose Constructions From Teflon TFE Fluorocarbon Resins", *Dupont Tech Services Laboratories*, Ribbans, TR #138.

"Percutaneous Insertion of a Permanent Transvenous Pacemaker Electrode through the Subclavian Vein", *Can. J. Sur.*, Friesen et al., 3-77, pp. 131-135.

"Eine Neue Methode Zur Perkutanen Implantation Permaneter Herz Schritt Macher" Sterz et al.

"Teflon, Tetrafluorethylene Resin, Extrusion of Thin Wall Tubing" *DuPont Information Bulletin*, No. X-81a, pp. 1-11.

*Primary Examiner*—T. J. Wallen

[57] ABSTRACT

This invention relates to a flexible cannula comprising material which tears readily in a longitudinal direction and can thus be easily removed by pulling tabs on opposite sides of the cannula apart after the catheter or other device has been inserted into the body.

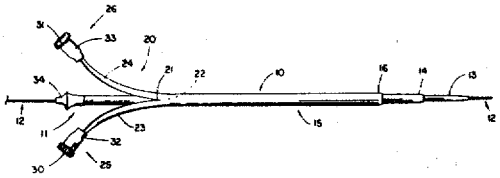

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–16 is confirmed.

* * * * *